(12) United States Patent
Druma

(10) Patent No.: US 9,351,779 B2
(45) Date of Patent: May 31, 2016

(54) EXPANDABLE DEVICE AND METHODS OF USE

(71) Applicant: KYPHON SARL, Neuchatel (CN)

(72) Inventor: Calin Druma, San Jose, CA (US)

(73) Assignee: KYPHON SÀRL, Neuchâtel (CH)

( * ) Notice: Subject to any disclaimer, the term of this patent is extended or adjusted under 35 U.S.C. 154(b) by 2 days.

(21) Appl. No.: 13/750,621

(22) Filed: Jan. 25, 2013

(65) Prior Publication Data

US 2014/0214085 A1    Jul. 31, 2014

(51) Int. Cl.
| | | |
|---|---|---|
| A61B 17/58 | (2006.01) | |
| A61B 17/60 | (2006.01) | |
| A61F 2/00 | (2006.01) | |
| A61B 17/88 | (2006.01) | |

(52) U.S. Cl.
CPC .................................. *A61B 17/8855* (2013.01)

(58) Field of Classification Search
CPC ......... A61F 2/4611; A61F 2/442; A61F 2/00; A61M 25/00; A61M 25/10; A61M 25/0119; A61M 25/1002; A61M 2025/1065; A61B 17/58; A61B 17/60
USPC .................................. 606/99, 105, 191–192; 623/17.11–17.16
See application file for complete search history.

(56) References Cited

U.S. PATENT DOCUMENTS

| | | | | |
|---|---|---|---|---|
| 4,271,839 | A * | 6/1981 | Fogarty et al. | 606/194 |
| 4,338,942 | A * | 7/1982 | Fogarty | 606/194 |
| 4,467,816 | A * | 8/1984 | Schluter et al. | 600/569 |
| 4,526,175 | A * | 7/1985 | Chin et al. | 606/192 |
| 4,969,888 | A | 11/1990 | Scholten et al. | |
| 5,364,345 | A * | 11/1994 | Lowery et al. | 604/500 |
| 5,383,889 | A * | 1/1995 | Warner et al. | 606/192 |
| 5,827,289 | A | 10/1998 | Reiley et al. | |
| 6,616,678 | B2 * | 9/2003 | Nishtala et al. | 606/198 |
| 8,052,710 | B2 * | 11/2011 | Kambin et al. | 606/192 |
| 8,066,689 | B2 * | 11/2011 | Mitelberg et al. | 604/509 |
| 2002/0147497 | A1 * | 10/2002 | Belef et al. | 623/17.12 |
| 2003/0028251 | A1 * | 2/2003 | Mathews | 623/17.16 |
| 2003/0105508 | A1 | 6/2003 | Johnson et al. | |
| 2003/0191489 | A1 | 10/2003 | Reiley et al. | |
| 2004/0010263 | A1 * | 1/2004 | Boucher et al. | 606/99 |
| 2005/0065609 | A1 * | 3/2005 | Wardlaw | 623/17.12 |
| 2005/0090901 | A1 * | 4/2005 | Studer | 623/17.12 |
| 2006/0195115 | A1 | 8/2006 | Ferree | |
| 2006/0271061 | A1 * | 11/2006 | Beyar et al. | 606/105 |
| 2006/0282152 | A1 * | 12/2006 | Beyerlein et al. | 623/1.11 |
| 2006/0293750 | A1 * | 12/2006 | Sherman et al. | 623/17.12 |
| 2007/0055300 | A1 | 3/2007 | Osorio et al. | |
| 2007/0162136 | A1 * | 7/2007 | O'Neil et al. | 623/17.12 |

(Continued)

FOREIGN PATENT DOCUMENTS

| | | |
|---|---|---|
| WO | 2006019626 A2 | 2/2006 |
| WO | 2012125184 A1 | 9/2012 |

*Primary Examiner* — Eduardo C Robert
*Assistant Examiner* — Michelle C Eckman
(74) *Attorney, Agent, or Firm* — Sorell Lenna & Schmidt LLP

(57) ABSTRACT

A surgical system including an expandable device is provided, including an inflatable body, an inner shaft and an outer shaft. The inflatable body has at least one folded segment, which are housed in a distal portion of the outer shaft. The inflatable body is tethered to a portion of the outer shaft. The inner shaft is affixed to a portion of the inflatable body, and is configured to control an axial and/or a radial inflation pattern of the folded inflatable body.

20 Claims, 8 Drawing Sheets

(56) References Cited

U.S. PATENT DOCUMENTS

| | | |
|---|---|---|
| 2007/0173924 A1* | 7/2007 | Gelbart et al. ............... 623/1.15 |
| 2008/0058931 A1 | 3/2008 | White et al. |
| 2008/0188805 A1* | 8/2008 | Davies et al. ............ 604/103.06 |
| 2009/0112323 A1* | 4/2009 | Hestad et al. .............. 623/17.12 |
| 2009/0299373 A1 | 12/2009 | Sisken |
| 2009/0299401 A1* | 12/2009 | Tilson ........................... 606/192 |
| 2009/0306700 A1 | 12/2009 | Miyata et al. |
| 2010/0262240 A1* | 10/2010 | Chavatte et al. ............ 623/17.11 |
| 2011/0137317 A1* | 6/2011 | O'Halloran et al. ............. 606/92 |
| 2011/0213400 A1* | 9/2011 | Ahmann et al. ............... 606/191 |
| 2012/0010713 A1* | 1/2012 | O'Halloran et al. ........ 623/17.12 |
| 2012/0022574 A1* | 1/2012 | Mafi et al. ..................... 606/198 |
| 2012/0059317 A1 | 3/2012 | Michiyo et al. |
| 2012/0071825 A1 | 3/2012 | Cisko, Jr. |
| 2012/0259355 A1* | 10/2012 | Druma et al. .................. 606/192 |
| 2013/0046332 A1* | 2/2013 | Jones et al. ................... 606/200 |

* cited by examiner

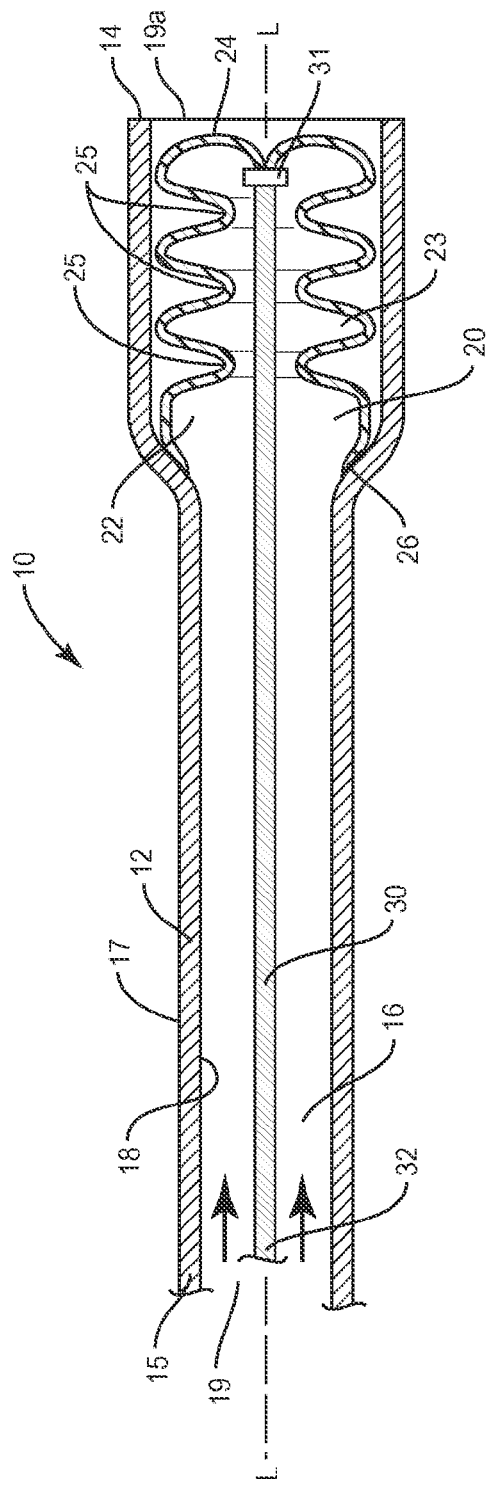
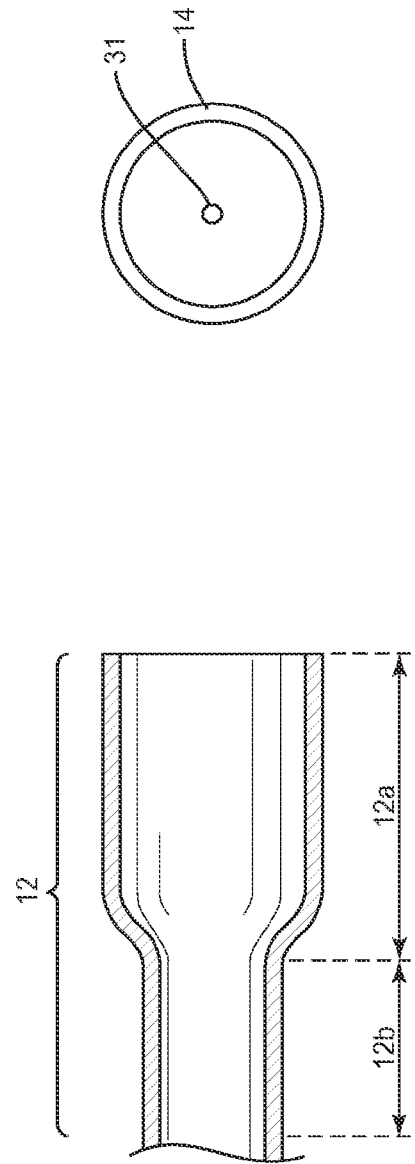
FIG. 1
FIG. 2
FIG. 3

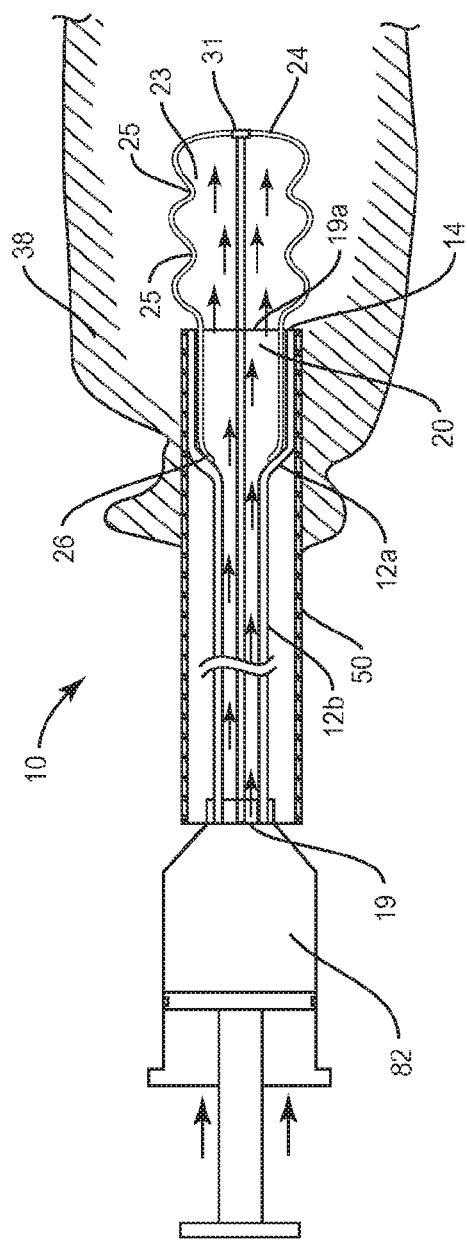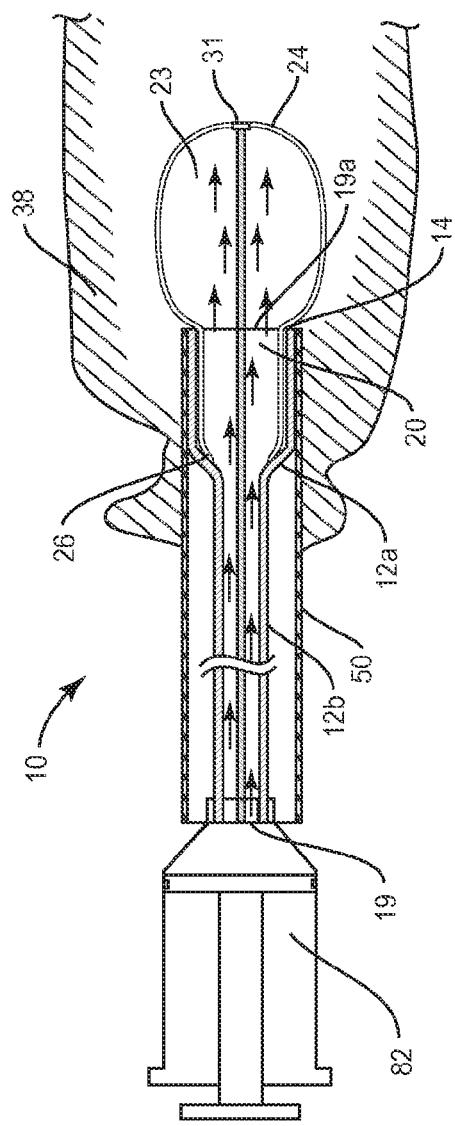
FIG. 4
FIG. 5

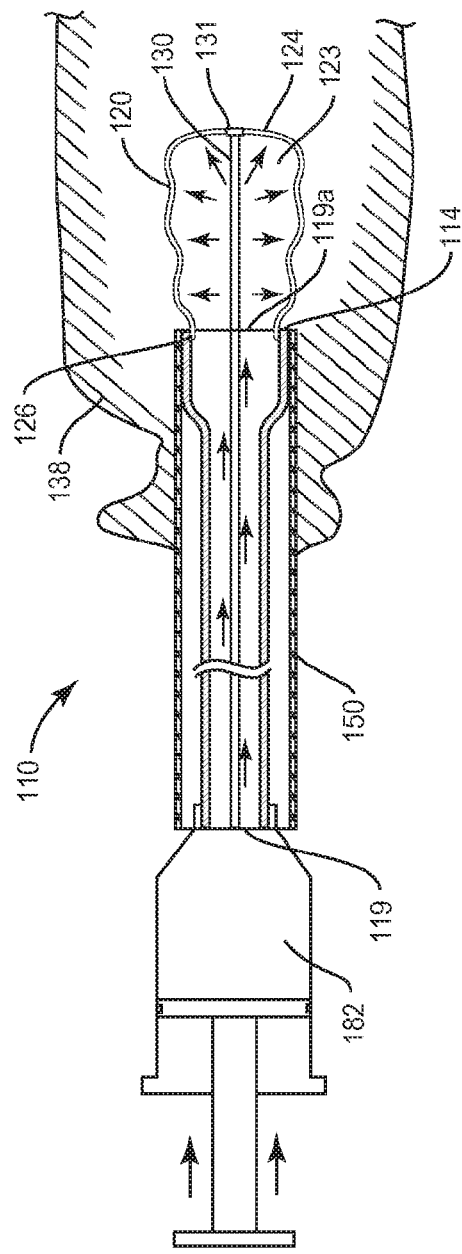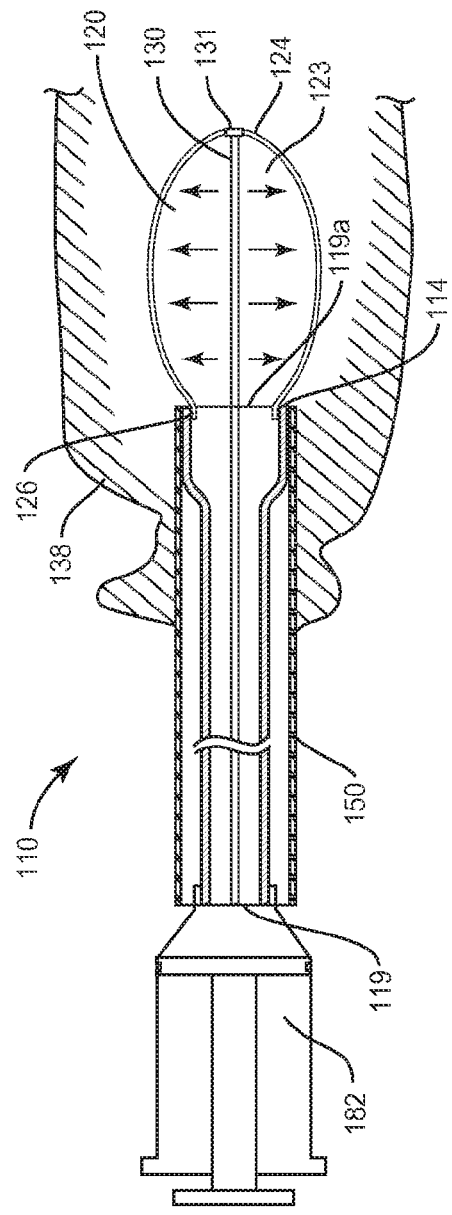

EXPANDABLE DEVICE AND METHODS OF USE

TECHNICAL FIELD

The present disclosure relates generally to instruments and devices for spinal surgery, more particularly to expandable devices including a self-extending folded inflatable body affixed to a portion of an outer shaft and a portion of an inner shaft. Methods of using such devices are also provided.

BACKGROUND

Height loss is commonly associated with spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing bone cement with balloon catheter technology. The kyphoplasty procedure restores height of the collapsed spinal bone which diminishes associated back pain.

In a kyphoplasty procedure, an inflatable balloon tamp (IBT) is inserted inside a fractured vertebral body. The IBT is inflated to separate the vertebra and create a cavity that is filled with bone cement to maintain the height correction.

Currently, in a kyphoplasty procedure, the IBT is typically stored or inserted in a cannula sized for the balloon with a diameter of the cannula of a sufficient width to accommodate the balloon in its entirety. Because the kyphoplasty requires an insertion into tissue, it is desirable to reduce the outer diameter of the cannula without negatively impacting the insertion forces of the IBT.

SUMMARY

This application provides a self-extending expandable device, an expandable device system and a method for treating fractures/lesions in bone. In accordance with the principles of the present disclosure, the self-extending expandable device includes an inflatable body, an inner shaft, and outer shaft. The inflatable body has at least one folded segment, which is housed in a distal portion of the outer shaft. The inflatable body is tethered to the outer shaft, and the inner shaft is affixed to a portion of the inflatable body. The inner shaft is configured to control an axial and/or a radial inflation pattern of the folded inflatable body. The inflatable body is configured to move from a deflated configuration to an inflated configuration. In one aspect, the self-extending expandable device has a collapsed, at least partially axially folded configuration while in a deflated configuration. In the expanded configuration, the inflatable body is configured to expand outwardly through an open end of a distal tip of the outer shaft.

In one embodiment, the expandable device includes an inflatable body having at least one axially folded segment and an inner shaft and an outer shaft having a longitudinal axis. The outer shaft includes a proximal end, a distal end, and a cavity extending from the proximal end to the oppositely positioned distal end along the longitudinal axis. The distal end of the outer shaft forms a distal open portion of the cavity, and is configured to receive at least one axially folded segment of the inflatable body in a housing portion. The proximal end of the outer shaft forms a proximal open portion of the cavity. A portion of the inflatable body is tethered to the outer shaft, and the inner shaft is positioned within the cavity, with the distal end of the inner shaft affixed to the inflatable body.

The device is configured for insertion through a cannula into a bone adjacent a fracture so that it can be used to realign bone fragments misaligned due to a bone fracture and/or to reestablish height to a collapsed part of the bone. The orientation of the folding of the inflatable body impacts the initial direction in which the expandable device self-extends. In one embodiment, the folding of the inflatable body provides a self-extending projection of the inflatable body into the bone upon being inflated. It is contemplated that the location at which the inflatable body is affixed to the inner shaft can contribute to a pattern of self-extension of the inflatable body.

In another embodiment, the expandable device is a self-extending folded inflatable body tethered to a portion of an outer shaft having a tubular portion and a housing portion, the inflatable body being affixed to a distal tip of an inner shaft. The housing portion is located at the distal end of the outer shaft, and is configured with a bump having a diameter larger than the diameter of the tubular portion. The inflatable body has a plurality of axially folded segments positioned in the housing portion of the outer shaft. In one embodiment, the expandable device may be included in a kit where the folded segments are pre-packed with a specific orientation in the housing portion of the outer shaft.

In yet another embodiment, a method for treating a bone fracture or bone lesion using an expandable device is provided, the method comprising: accessing a bone; inserting into the bone an expandable device having an outer shaft, an inner shaft, and a balloon positioned in a housing portion of the outer shaft; inflating the balloon with a liquid or gas wherein the balloon is configured to self-extend in an axial dilation; locking the inner shaft in a position within the expandable device wherein the locked inner shaft is configured to stop the balloon from further axial dilation; inflating the balloon with an additional amount of liquid or gas, the locked inner shaft being configured to cause the balloon to extend in a radial dilation; creating a void in the bone with the inflated balloon; deflating the balloon and removing the expandable device from the bone; inserting a bone void filler into the void; and allowing the inserted bone void filler to harden. The balloon comprises a proximal portion bonded to the outer shaft, a distal portion bonded to a portion of the inner shaft, and at least one axially folded segment. The balloon is configured to substantially clear debris resulting from a fracture from a cortical bone by pushing the debris to a cortical bone wall. It is further contemplated that the fractured bone to be treated can be a vertebral body.

In another embodiment, an expandable system includes a cannula comprising an expandable device having an outer shaft, an inner shaft, and a balloon positioned in a housing portion of the outer shaft. The balloon has a proximal portion bonded to the outer shaft, a distal end bonded to the inner shaft, and at least one axially folded segment. A method of using such an expandable device for treatment of a fractured bone is also contemplated. It is contemplated that an outer diameter of the cannula can be reduced with the expandable device without negatively impacting insertion forces.

BRIEF DESCRIPTION OF DRAWINGS

The present disclosure will become more readily apparent from the specific description accompanied by the following drawings.

FIG. 1 is a side, cross-sectional view of an expandable device in accordance with the principles of the disclosure;

FIG. 2 is a side, cross-sectional view of a component of the expandable device shown in FIG. 1;

FIG. 3 is a is a cross-sectional view of a distal end of a component of the expandable device shown in FIG. 1;

FIG. 4 plan view, in cross-section, of the expandable device shown in FIG. 1 disposed with a vertebra;

FIG. 5 is a plan view, in cross-section, of the expandable device shown in FIG. 1 disposed with a vertebra;

FIG. 11 is a plan view, in cross-section, of the expandable device shown in FIG. 10 disposed with a vertebra; and FIG. 12 is a plan view, in cross-section, of the expandable device shown in FIG. 10 disposed with a vertebra.

Like reference numerals indicate similar parts throughout the figures.

DETAILED DESCRIPTION

Figure 6A:
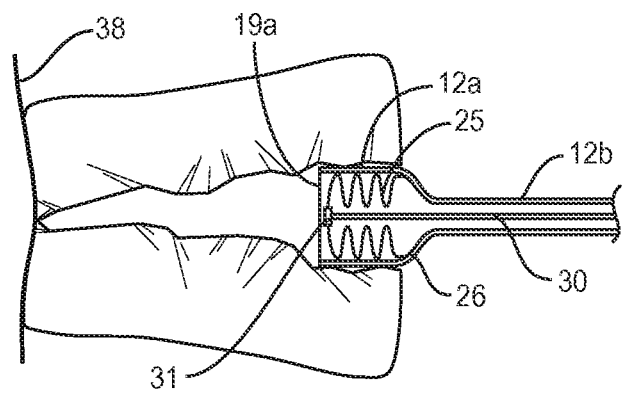
FIG. 6A is a plan view, in cross-section, of the expandable device shown in FIG. 1 disposed with a vertebra.

An apparatus and method are described for a self-extending expandable device including an inflatable body; an inner shaft, and outer shaft, at least a segment of the inflatable body folded and housed in a distal portion of the outer shaft, a portion of the inflatable body tethered to a portion of the outer shaft, and the inner shaft affixed to the distal end of the inflatable body. For illustrative purposes, the device, system, and method shall be described in the context of positioning an inflatable body and the use of bone void filler in a vertebral body of a patient to treat vertebral compression fractures, although the apparatus and methods can be used to treat other conditions. The inner shaft may be fabricated with biologically compatible materials fabricated from biologically acceptable materials suitable for medical apparatuses and having a suitable flexibility, including silicone, chloroprene, thermoplastic polyurethane (TPU), polyethylene terephtalate (PET), or polyamide (Nylon). A preferred material for fabrication of the inner shaft is Nylon.

It is envisioned that the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, postero-rior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for treating fractures, including an inflation source, an inflatable bone tamp (IBT), employing drills and delivering bone void filler, such as, for example, autograft, allograft, demineralized bone matrix, mineral composites, blocks, granules and pellets and bone cement, such as, for example, polymethylmethacrylate (PMMA)-based material (Kyphon HV-R, ActivOs, ActivOs 10, Xpede), calcium phosphate (Skaffold, Norian, Hydroset, KyphOs FS) and calcium sulfate (OsteoSet), as well as other injectables. In one embodiment, the bone void filler is bone cement, preferably a material comprising polymethylmethacrylate (PMMA). The disclosure also includes a description of related methods of employing an expandable device including the inflatable body, inner shaft and outer shaft in accordance with the principles. Alternate embodiments are also disclosed. Reference will now be made in detail to the exemplary embodiments of the present disclosure, which are illustrated in the accompanying figures. Turning now to FIGS. 1-12, there are illustrated components of a self-extending expandable device and method in accordance with the principles of the present disclosure.

The components of the disclosed system can be fabricated from biologically acceptable materials suitable for medical applications, including metals, synthetic polymers, ceramics and bone material and/or their composites, depending on the particular application and/or preference of a medical practitioner. For example, the components of the disclosed system, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the disclosed system may have material composites, including the above materials, to achieve various desired characteristics such as strength, rigidity, elasticity, compliance, biomechanical performance, durability and radiolucency or imaging preference. The components of the disclosed system, individually or collectively, may also be fabricated from a heterogeneous material such as a combination of two or more of the above-described materials. The components of the disclosed system may be monolithically formed, integrally connected or include fastening elements and/or instruments, as described herein.

The disclosed system includes an expandable device 10 including an outer shaft 12 having a longitudinal axis L. Outer shaft 12 includes distal end 14, a proximal end 15, and cavity 16 extending between proximal end 15 and distal end 14 along the longitudinal axis L. Cavity 16 is defined by outer wall 17 and inner wall 18. End 14 of the outer shaft 12 forms a distal end of the cavity 16, and end 15 of the outer shaft 12 forms a proximal end of the cavity 16. Opening 19 at end 15 provides a continuous hollow space in cavity 16 to end 14 where the distal end of the cavity 16 forms opening 19a.

In one embodiment, cavity 16 is configured to receive an inflatable body 20. Inflatable body 20 has a distal end 24 and a tethered end 26. End 26 is tethered to inner wall 18 of shaft 12. Body 20 includes lumen 22 extending from and through the tethered end 26 to the oppositely disposed distal end 24 of the inflatable body 20. Lumen 22 is in communication with fillable cavity 23, which is located at the distal end of the cavity 16. Body 20 may be configured to expand outward in all directions from cavity 23 or alternatively be configured to expand in only one direction from cavity 23 such that cavity 23 is compliant with a predetermined form. The outer shaft 12 includes a housing portion 12a at the distal portion which houses the inflatable body 20. Portion 12a is bumped out to provide a wider diameter than tubular portion 12b. Portion 12a is configured to store at least a portion of body 20 in a deflated configuration. In one embodiment, body 20 is fully enclosed in cavity 16. In another embodiment the distal end portion 12a is not bumped out and provides a diameter equal to or less than the tubular portion 12b.

When in a deflated configuration, body 20 includes at least one fold 25. The folds can take a multitude of forms, such as, for example, crinkles, creases, ruffles, pleats, tucks or other such gathered segments. Body 20 is configured to expand when inflated, with end 26 being tethered to inner wall 18 and end 24 positioned at the open end 19a. In one embodiment, body 20 is folded axially inside portion 12a. In other embodiments, body 20 can be folded longitudinally inside portion 12a or unfolded entirely.

In the disclosed system, expandable device 10 includes inner shaft 30 positioned within cavity 16, the inner shaft 30 having distal end 31 and proximal end 32. In one embodiment, distal end 31 is affixed to end 24 of balloon 20. In other embodiments, distal end 31 is affixed to other portions of body 20. In accordance with an embodiment, end 31 is affixed to body 20 such that shaft 30 is free to move at proximal end 32 to allow for extension of the inflatable body 20.

End 26 can be tethered to the outer shaft 12 by any method of bonding or attachment, such as, for example, adhesive bonding or thermal bonding. In one embodiment, slack in the inflatable body 20 is provided by the inner shaft 30, the slack being configured to facilitate self-expansion of expandable device 10. In one embodiment, the slack of shaft 30 is configured to extend body 20 out of portion 12a. End 31 is affixed to a portion of distal end 24 by any method of bonding or attachment, such as, for example, adhesive bonding or thermal bonding, with thermal bonding preferred in one embodiment. Expansion of body 20 may be limited by the amount of slack of the inner shaft 30 as affixed to end 24. In one embodiment, once a desired length of an inflated configuration of body 20 is achieved, inner shaft 30 is locked in place such that body 20 may be further pressurized and expand radially. Cavity 23 may be expanded with contrast liquid using x-ray control or other such material that may be monitored to determine the degree of expansion of device 10 once inserted into tissue.

The outer shaft 12 can be inserted into a patient in a surgical procedure once an access hole to a desired location is prepared using instruments typical of a balloon kyphoplasty procedure. In one embodiment, the outer shaft 12 is inserted into the access hole in a bone, leading with the distal end 14 of the outer shaft, as shown in FIG. 1.

In another embodiment, the surgical system disclosed may include expandable device 10, a filling apparatus 82, and a cannula 50. Filling apparatus 82 can be a high pressure syringe or any other device configured to deliver a liquid or gas to inflatable body 20. In one embodiment, the filling apparatus 82 is configured to engage device 10 at proximal opening 19 deliver liquid or gaseous material into body 20 in a pressurized state. Body 20 is configured to self-expand through distal opening 19a upon receiving the liquid or gaseous material from apparatus 82. Body 20 is in communication with cavity 16, lumen 22, and a lumen of apparatus 82. The material flowing from apparatus 82 inflates cavity 23 of body 20 and outwardly expands such that the fold 25, or plurality of folds 25, unfold and extend into tissue 38 to be treated by expandable device 10.

In one embodiment, pressure that builds in body 20 propels end 24 forward into a hole in the prepared tissue 38. In one embodiment, when body 20 contains axial folds, cavity 23 expands longitudinally through axial dilation in a first step such that fold 25, or a plurality of folds 25, extend through opening 19a. If body 20 contains both folds, the body 20 propels in an axial direction first and then in a radial motion thereafter. Each fold 25 sequentially extends through opening 19a in the first step of the self-expansion along longitudinal axis L. In one embodiment, the axial dilation of body 20 is limited by shaft 30 affixed at distal end 31. End 26 remains tethered to portion 12a during the self-expansion of device 10. In one embodiment, the second step in the self-expansion of body 20 is a radial extension of cavity 23. In such an embodiment, cavity 23 may be configured to have a balloon shape.

Cannula 50 provides a channel from proximal opening 19 to distal opening 19a. Cannula 50 also provides a protected access port to tissue 38. In one embodiment, cannula 50 includes a plurality of different shapes or combinations of cross-sectional shapes. The components of cannula 50 can be fabricated from biologically acceptable materials suitable for medical apparatuses, including metals, synthetic polymers, ceramics, thermoplastic and polymeric material and/or their composites. For example, the components of the cannula 150, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan, Fe—Mn—Si and Fe—Ni—Co—Ti composites), ceramics and composites thereof such as calcium phosphate (e.g., SKELITE™ manufactured by Biologix™, Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers based materials, polymeric rubbers, polyolefin rubbers, semi-rigid and rigid materials, thermoplastic elastomers, thermoset elastomers, elastomeric composites, rigid polymers including polyphenylene, polyamide, polyimide, polyetherimide, polyethylene, epoxy, polyacrylate and composites of metals and calcium-based ceramics, composites of PEEK and calcium based ceramics, and combinations of the above materials. Various components of cannula 50 may have material composites, including the above materials, to achieve various desired characteristics such as strength, rigidity, elasticity, compliance, and biomechanical performance, durability and to provide a non-stick surface. The components of cannula 50 may be monolithically formed, integrally connected or include fastening elements and/or coupling components, as described herein. The cannulas as described herein may be disposable or may be autoclavable or resterilizable. The cannulas and accessories may be part of a kit that includes expandable device 10.

Figure 6B:
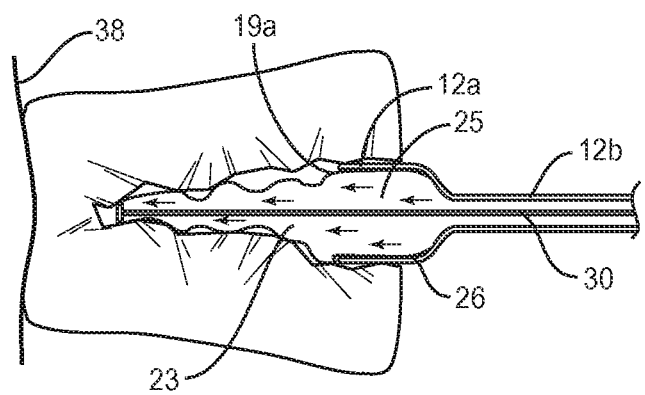
FIG. 6B is a plan view, in cross-section, of the expandable device shown in FIG. 1 disposed with a vertebra.
Figure 6C:
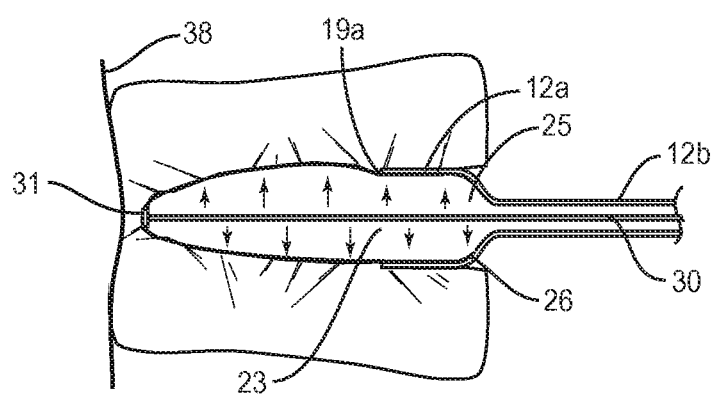
FIG. 6C is a plan view, in cross-section, of the expandable device shown in FIG. 1 disposed with a vertebra.
Figure 6D:
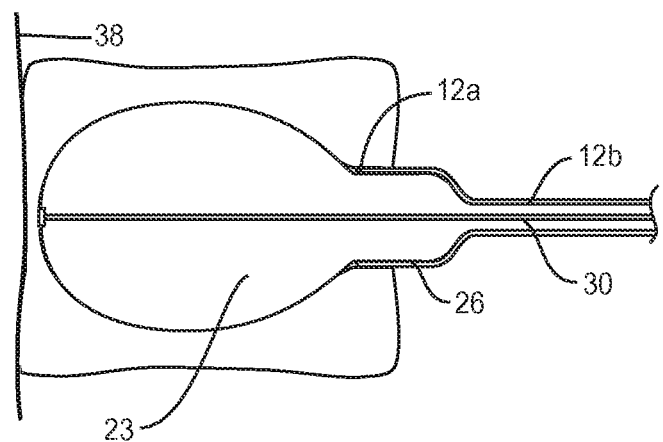
FIG. 6D is a plan view, in cross-section, of the expandable device shown in FIG. 1 disposed with a vertebra.
Figure 6E:
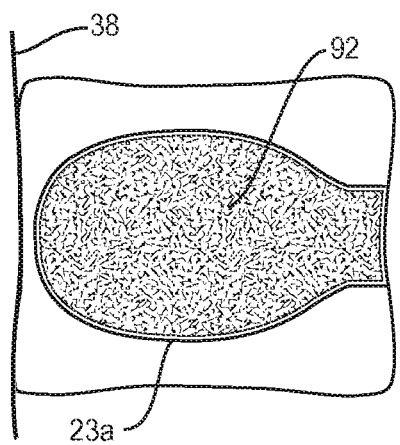
FIG. 6E is a plan view, in cross-section, of the expandable device shown in FIG. 1 disposed with a vertebra.
Figure 7:
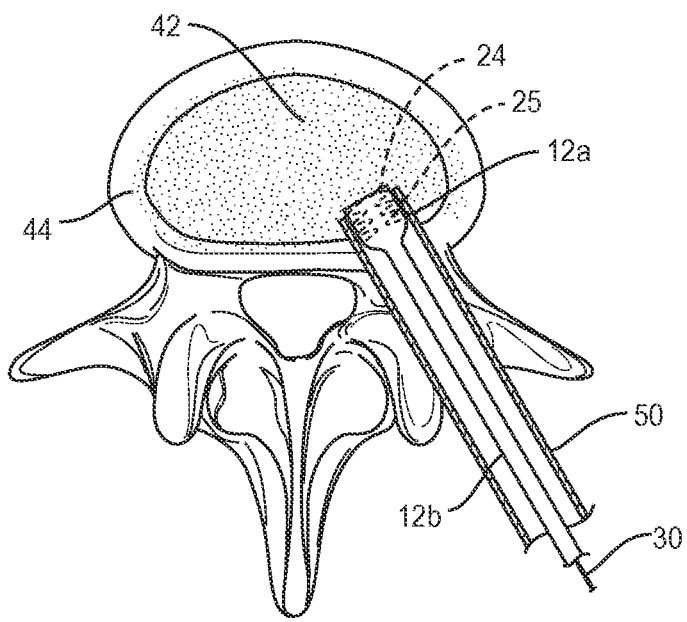
FIG. 7 is a plan view, in cross-section, of the expandable device shown in FIG. 1 disposed with a vertebra.
Figure 8:
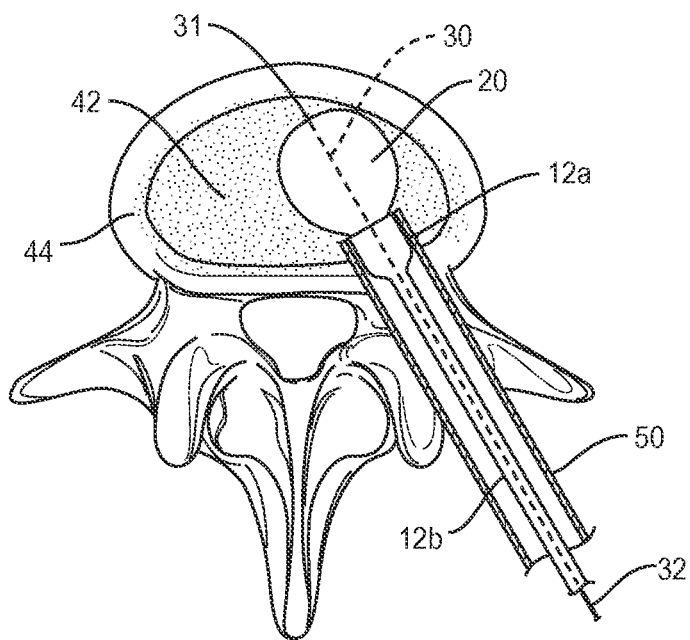
FIG. 8 is a plan view, in cross-section, of the expandable device shown in FIG. 1 disposed with a vertebra.

It is envisioned that the disclosed system, including expandable device 10, may be used in a surgical method in accordance with the present principles of the disclosure. As shown in FIG. 6A, prior to a self-expansion of device 10, a portion of opening 19a is positioned in a vertebral body 38. A plurality of folds 25 are positioned in portion 12a with axial folding, with end 26 being tethered to portion 12a. As shown in FIG. 6B, in a first step of self-expansion of device 10, pressurized liquid or gas is pumped from apparatus 82 into opening 19 such that folds 25 of body 20 are extended in a longitudinal direction beyond opening 19. Injection of the liquid or gas may be automated or controlled by a medical practitioner performing the surgery. As shown in FIG. 6C, in the second step of self-expansion, once axial dilation reaches a predetermined boundary, the fillable cavity is configured to dilate radially. As shown in FIG. 6D, cavity 23 is configured to expand to a balloon shape once the self-expansion such that body 20 substantially clears debris resulting from a fracture from a cortical bone by pushing the debris to a cortical bone wall. Prior to being withdrawn, body 20 is deflated such that it leaves void 23a in vertebral body 38 once device 10 is removed. Inflation and deflation of body 20 may be repeated as many times as necessary to create a satisfactory void in vertebral body 38. After device 10 is withdrawn from vertebral body 38, void 23a is filled with bone void filler 92 that cures to a hardened state.

Figure 9:
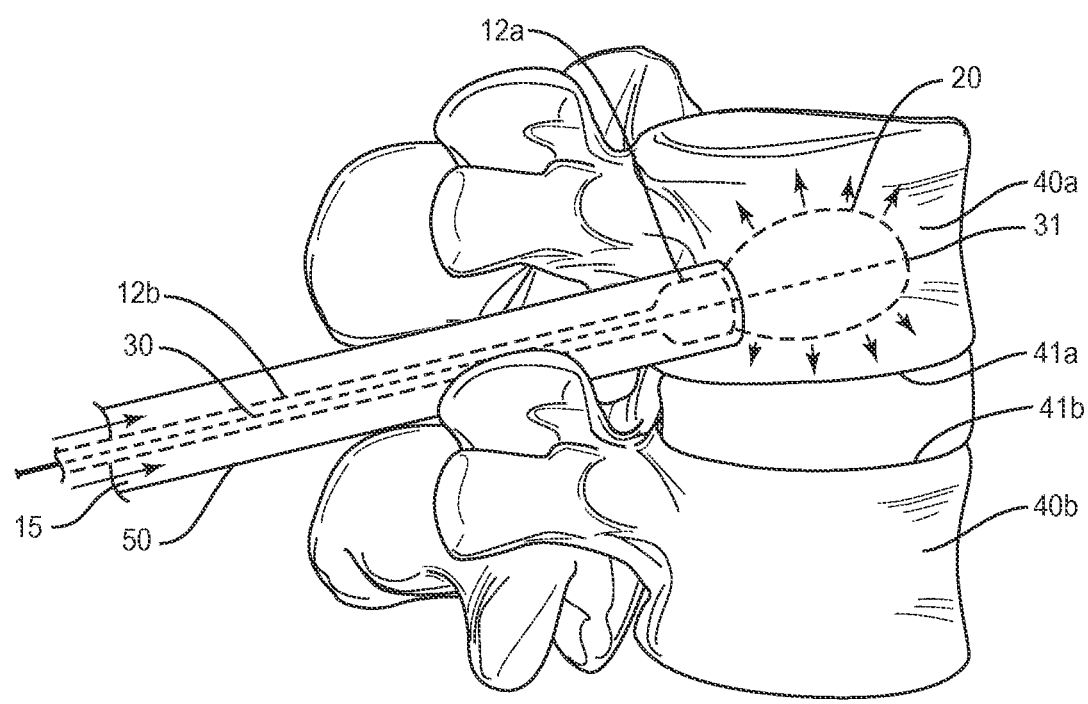
FIG. 9 is a plan view, in cross-section, of the expandable device shown in FIG. 1 disposed between two vertebrae.
Figure 10:
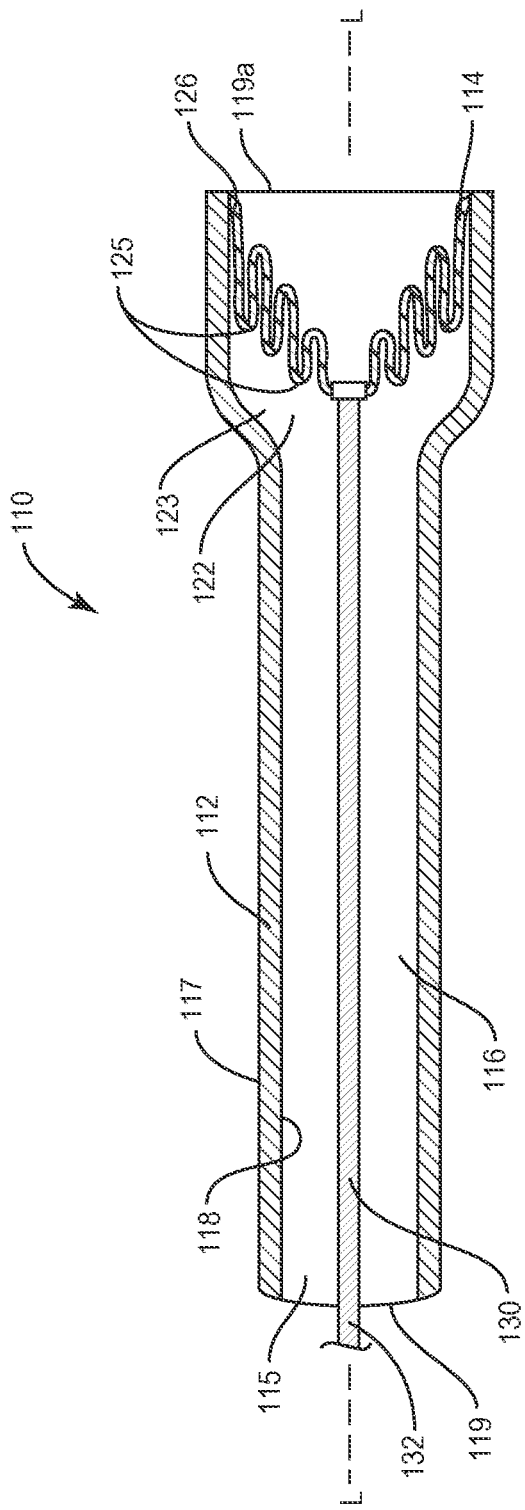
FIG. 10 is a side, cross-sectional view of an expandable device in accordance with the principles of the disclosure.

Portion 12a is positioned in vertebral disc space 42 of a vertebral body. The disc space 42 has a nucleus that is surrounded by an annulus 44. While in the expanded configuration, body 20 has end 31 opposite end 32 with inner shaft 30 extending the length of the expandable device. As shown in FIG. 9, the subject vertebral disc space is located between an upper vertebra 40a having an inferior endplate 41a and a lower vertebra 40b having a superior endplate 41b. When body 20 is in the inflated state inferior endplate 41a is separated from inferior endplate 41b. Cannula 50 provides an access port into a vertebral body, cannula 50 having included therein an outer shaft extending from the proximal end 15 through the distal end 14 of device 10.

In another embodiment, the disclosed system includes an expandable device 110 including an outer shaft 112 having a longitudinal axis L. Outer shaft 112 includes distal end 114, a proximal end 115, and cavity 116 extending between proximal end 115 and distal end 114 along the longitudinal axis L. Cavity 116 is defined by outer wall 117 and inner wall 118. End 114 forms a distal end of cavity 116, and end 115 forms a proximal end of cavity 116. Opening 119 at end 115 provides a continuous hollow space in cavity 116 to end 114 where the distal end of the cavity 116 forms opening 119a.

Inflatable body 110 contains longitudinal folds 125 or a plurality of longitudinal folds 125, when in a deflated configuration. In this configuration, an inner shaft 130 has a proximal end 132 and a distal end 131. Shaft 130 is positioned within cavity 116 formed by the inner wall 118 and outer wall 117 of an outer shaft 112. The deflated longitudinal folds 125 of inflatable body 120 are tethered to the tip of the end 114 at tethered end 126. Alternatively, the tethering of body 120 can be accomplished by bonding tethering end 126 with the inner wall 118 of the outer shaft 112. In this embodiment, body 120 has an overall concave shape in the housing portion of shaft 612. Proximal end 124 of body 120 is affixed to end 131, which extends to the proximal end of shaft 112.

As shown in FIG. 11-12, end 131 is configured to limit the longitudinal extension of body 120. The self-expansion of body 120 can propel fillable cavity 123 outside opening 119a simultaneously in both a longitudinal and axial direction while body 120 remains tethered at end 126. As illustrated in the configuration shown in FIG. 12, fillable cavity 123 of body 120 can form a balloon shape once fully extended in the tissue.

Any tools typical of a balloon kyphoplasty may be utilized in preparing the patient tissue for the expandable device (e.g. 10) to be inserted, typically through a cannula. For example, a tocar or sharp-ended stylet can be inserted into the cannula for initially piercing tissue. The tocar or sharp-ended stylet is then removed and a drill used to prepare a hole into the desired location.

The expandable devices depicted in FIGS. 1-12 may take many forms and methods of treating fractures and bone lesions may include additional steps. It is contemplated that the expandable devices may be configured in a number of ways and include different shaped handle portions of the cannula, such as, for example, round, oval, oblong, square, rectangular, polygonal, irregular, uniform, non-uniform, offset, staggered, tapered, consistent or variable, depending on the requirements of a particular application. An outer surface of the handle portions of the cannulas may be rough, arcuate, undulating, mesh, porous, semi-porous, dimpled and/or textured according to the requirements of a particular application. The lumen that can be variously configured and have a cross-section that is, for example, round, oval, oblong, square, rectangular, polygonal, irregular, uniform, non-uniform, offset, staggered, tapered, consistent or variable, depending on the requirements of a particular application. In one embodiment, in accordance with the disclosure, it is contemplated that the cannulas include a cutting edge at a distal end configured to cut into the tissue. In the alternative, the distal end may include a threaded portion, fluted tip as well as other surgical configurations. In another alternative, a separate device can be used to cut a primary access port for the cannula (e.g., a trocar).

In assembly and use, the expandable devices are employed in a surgical procedure for treatment of a disorder affecting a section of bone, such as a fracture, for example in the distal radius, tibial plateau or proximal humerus of a patient, as described herein. In use, to treat the affected section, a medical practitioner obtains access to the bone in any appropriate manner, which may include incision and retraction of tissues. Once the bone is exposed the expandable devices can be inserted through any appropriate access port adjacent to a fracture to be treated. It is envisioned that expandable devices can be used in any existing surgical method or technique including open surgery, mini-open surgery, minimally invasive surgery and percutaneous surgical implantation, whereby the site is accessed through a micro-incision, or sleeve that provides a protected passageway to the area. Once access to the surgical site is obtained, the expandable device can be deployed so create a void for bone cement or other bone void filler, to treat the condition, such as repair the fracture.

It is contemplated that the bone void filler can include other agents and materials that can be delivered to the surgical site using the expandable device. These agents include therapeutic polynucleotides or polypeptides. It is further contemplated that these agents may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite (HA), calcium phosphate and calcium sulfate, biologically active agents, for example, gradual release compositions such as by blending in a bioresorbable polymer that releases the biologically active agent or agents in an appropriate time dependent fashion as the polymer degrades within the patient. Suitable biologically active agents include, for example, Bone Morphogenetic Proteins (BMP), Growth Differentiation Factors (GDF) and cytokines. The material components of can be made to include radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An expandable device including:
   an inflatable body defining a longitudinal axis;
   an inner shaft having a closed distal end; and
   an outer shaft comprising a rigid material, the inflatable body having a folded segment comprising a bellows configured to expand and contract a length of said folded segment along said longitudinal axis, said folded segment housed in a distal portion of the outer shaft, the inflatable body comprising a proximal end tethered to a portion of an inner wall of the outer shaft and a distal end affixed to the closed distal end of the inner shaft, the inner shaft being free-floating within the outer shaft such that said inner shaft is free of any connection to said outer shaft and configured to control an axial and/or a radial inflation pattern of the folded inflatable body.

2. An expandable device according to claim 1, wherein the inflatable body has a collapsed configuration and an expanded configuration, wherein in the expanded configuration, the inflatable body is configured to self-extend outside of an open end of a distal tip of the outer shaft.

3. An expandable device according to claim 2, wherein the inner shaft has a maximum length defined by a distance between a proximal end surface of the inner shaft and an opposite distal end surface of the inner shaft, the maximum length being coaxial with the longitudinal axis when the inflatable body is in both the collapsed and expanded configurations.

4. An expandable device according to claim 2, wherein:
   the outer shaft has a tubular portion and a housing portion that includes the distal tip;
   the inflatable body is positioned entirely within the housing portion when in the collapsed configuration such that the distal end of the inflatable body is positioned between the proximal end of the inflatable body and the open end.

5. An expandable device according to claim 1, wherein the inflatable body has a plurality of bellows.

6. An expandable device according to claim 1, wherein the outer shaft has a tubular portion and a housing portion.

7. An expandable device according to claim 6, wherein the inflatable body is positioned in the housing portion.

8. An expandable device according to claim 6, wherein a diameter of the housing portion is larger than a diameter of the tubular portion of the outer shaft, the expandable device being tapered from the housing portion to the tubular portion.

9. An expandable device according to claim 1, wherein the closed distal end of the inner shaft comprises a distal end surface that extends perpendicular to and intersects the longitudinal axis.

10. An expandable device according to claim 1, wherein the inner shaft has a maximum length defined by a distance between a proximal end surface of the inner shaft and an opposite distal end surface of the inner shaft, the maximum length being coaxial with the longitudinal axis.

11. An expandable device according to claim 1, wherein:
the outer shaft has a tubular portion and a housing portion; and
the outer shaft is tapered between the housing portion and the tubular portion, the housing portion and the tubular portion being coaxial with one another.

12. An expandable device according to claim 1, wherein the inner shaft extends between a proximal end surface and the closed distal end, the closed distal end having a distal end surface that extends parallel to the proximal end surface, the inner shaft having an intermediate portion midway between the proximal and distal end surfaces, the inner shaft having a uniform diameter from the proximal end surface to the intermediate portion.

13. An expandable device system comprising:
a cannula; and
an expandable device comprising:
an outer shaft having a housing portion and a tubular portion that are each positioned within the cannula;
an inner shaft having a proximal portion and a distal portion having a closed distal end, the inner shaft being free-floating within the outer shaft such that said inner shaft is free of any connection to said outer shaft; and
a balloon configured to create a void within a bone upon inflation of the balloon, the balloon extending along a longitudinal axis between proximal and distal ends thereof, the balloon positioned in the housing portion of the outer shaft, the proximal end of the balloon bonded to an inner surface of the housing portion of the outer shaft, said balloon having a distal end bonded to the closed distal end of the inner shaft, the balloon having a folded segment comprising a bellows, the housing portion having a larger diameter than the tubular portion of the outer shaft, the expandable device being tapered from the housing portion to the tubular portion.

14. An expandable device system according to claim 13, wherein the bellows is configured to expand a length of said folded segment along said longitudinal axis.

15. An expandable device system according to claim 13, wherein the bellows is configured to expand and contract a length of said folded segment along said longitudinal axis.

16. An expandable device system according to claim 13, wherein the bellows is configured to self-extend in an axial dilation upon an introduction of the pressurized fluid into the balloon, wherein the distal end of the inner shaft is configured to control the length of the axial dilation of the balloon.

17. A method for treating a bone fracture or bone lesion using an expandable device is provided, the method comprising:
accessing a bone;
inserting into the bone an expandable device having an outer shaft having a tubular portion and a housing portion, an inner shaft extending along a longitudinal axis between a closed distal end and a proximal end, and a deflated balloon positioned in the housing portion of the outer shaft, said inner shaft being free-floating within the outer shaft such that said inner shaft is free of any connection to said outer shaft, said balloon having a proximal portion bonded to an inner surface of the housing portion of the outer shaft, said balloon having a distal portion bonded to the closed distal end of the inner shaft, the balloon having an axially folded segment comprising a bellows configured to expand and contract a length of said folded segment along said longitudinal axis;
inflating said balloon with a pressurized fluid wherein the balloon is configured to self-extend in an axial dilation;
locking the inner shaft in a position within the expandable device wherein said locked inner shaft is configured to stop the balloon from further axial dilation;
inflating said balloon with an additional amount of the pressurized fluid, said locked inner shaft configured to cause the balloon to extend in a radial dilation;
creating a void in the bone with the inflated balloon;
deflating said balloon and removing said expandable device from the bone;
inserting a bone void filler into the void; and
allowing said inserted bone void filler to harden.

18. A method as recited in claim 17, wherein the balloon is configured to clear debris resulting from a fracture from a cortical bone by pushing the debris to a cortical bone wall.

19. A method as recited in claim 17, wherein the inner shaft is configured to control a pattern of self-extension of the balloon.

20. A method as recited in claim 17, wherein the balloon is compliant.

* * * * *